United States Patent
Madan et al.

(10) Patent No.: US 6,278,218 B1
(45) Date of Patent: Aug. 21, 2001

(54) APPARATUS AND METHOD FOR TUNING ULTRASONIC TRANSDUCERS

(75) Inventors: Ashvani K. Madan, Mason; Jean M. Beaupre, Blue Ash; Eitan T. Wiener, Cincinnati; Foster B. Stulen, Westerville, all of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/584,583

(22) Filed: May 31, 2000

Related U.S. Application Data

(62) Division of application No. 09/292,134, filed on Apr. 15, 1999.

(51) Int. Cl.$^7$ ................................................ H02N 2/00
(52) U.S. Cl. ................ 310/312; 310/323.12; 310/323.13
(58) Field of Search ........................... 310/312, 323.12, 310/323.13, 323.17, 323.18, 323.19

(56) References Cited

U.S. PATENT DOCUMENTS

| | | | |
|---|---|---|---|
| 2,651,148 | 9/1953 | Corwile | 239/102.2 |
| 2,870,521 | * 1/1959 | Rudnick | 310/312 |
| 2,990,616 | 7/1961 | Balamuth et al. | 228/1.1 |
| 3,992,760 | * 11/1976 | Roberts | 29/25.35 |
| 4,749,437 | * 6/1988 | Welter | 156/580 |
| 4,812,697 | * 3/1989 | Mishiro | 310/321.01 |
| 4,941,243 | * 7/1990 | Cleveland | 29/25.35 |
| 4,989,583 | 2/1991 | Hood | 128/24 A |
| 5,026,387 | 6/1991 | Thomas | 606/169 |
| 5,166,907 | * 11/1992 | Newnham et al. | 367/157 |
| 5,205,176 | * 4/1993 | Kibblewhite | 29/25.35 |
| 5,324,299 | 6/1994 | Davison et al. | 606/167 |
| 5,342,380 | 8/1994 | Hood | 606/169 |
| 5,417,672 | 5/1995 | Nito et al. | 604/283 |
| 5,465,468 | * 11/1995 | Manna | 29/25.35 |
| 5,630,420 | 5/1997 | Vaitekunas | 128/662.03 |
| 5,746,756 | 5/1998 | Bromfield et al. | 606/169 |
| 5,793,148 | * 8/1998 | Rabe | 310/325 |
| 5,798,599 | 8/1998 | Harwood | 310/325 |
| 5,879,363 | 3/1999 | Urich | 606/167 |
| 5,957,932 | * 9/1999 | Vaitekunas | 606/169 |
| 5,986,385 | * 11/1999 | Atsuta | 310/323 |
| 5,993,458 | 11/1999 | Vaitekunas et al. | 606/104 |
| 5,993,477 | 11/1999 | Vaitekunas et al. | 606/232 |
| 5,998,908 | * 12/1999 | Goodson | 310/325 |
| 6,204,592 | * 3/2001 | Hur | 310/323.18 |

FOREIGN PATENT DOCUMENTS

| | | |
|---|---|---|
| 0450578 B1 | 9/1996 | (EP) . |
| 145691 | 7/1921 | (GB) . |
| 868784 | 5/1961 | (GB) . |

OTHER PUBLICATIONS

Dukane Ultrasonis Division User Manual for a 40 kHz Probe and Convert a Probe System, 403–375A.

* cited by examiner

Primary Examiner—Thomas M. Dougherty
(74) Attorney, Agent, or Firm—Verne E. Kreger, Jr.

(57) ABSTRACT

A method of manufacturing high power sandwich type ultrasonic transducers and, more particularly, a new method of tuning high power sandwich type ultrasonic transducers without the need for a trimming process. A method in accordance with the present invention includes the steps of assembling a sandwich type ultrasonic transducer, measuring the resonant frequency of the ultrasonic transducer, and selecting from a plurality of tuning elements, whereby a dimension or material property of a selected tuning element alters the measured resonant frequency of the ultrasonic transducer to a desired resonant frequency after the tuning element is attached to the ultrasonic transducer.

2 Claims, 5 Drawing Sheets

APPARATUS AND METHOD FOR TUNING ULTRASONIC TRANSDUCERS

This Application is a division of Ser. No. 09/292,134 filed Apr. 15, 1999.

FIELD OF THE INVENTION

The present invention relates, in general, to apparatus and methods for manufacturing high power sandwich type ultrasonic transducers and, more particularly, to a new method of tuning high power sandwich type ultrasonic transducers.

BACKGROUND OF THE INVENTION

This application is related to the following copending patent applications: application Ser. No. 09/104,612 filed Jun. 25, 1998; application Ser. No. 09/104,789 filed Jun. 25, 1998; and application Ser. No. 09/104,648 filed Jun. 25, 1998, all assigned to the same assignee as the present invention and all of which are hereby incorporated herein by reference.

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy that may be transmitted from the ultrasonic transducer through the waveguide to the surgical end-effector. Such instruments are particularly suited for use in minimally invasive procedures, such as endoscopic or laparoscopic procedures, wherein the end-effector is passed through a trocar to reach the surgical site.

Ultrasonic vibration is induced in the surgical end-effector by, for example, electrically exciting a transducer which may be constructed of one or more piezoelectric or magnetostrictive elements in the instrument handpiece. Vibrations generated by the transducer section are transmitted to the surgical end-effector via an ultrasonic waveguide extending from the transducer section to the surgical end-effector.

Sandwich type ultrasonic transducers, also called Langevin transducers, are well known and established for the production of high intensity ultrasonic motion. In United Kingdom Patent No. 145,691, issued in 1921, P. Langevin inventor, a sandwich of piezoelectric material positioned between metal plates is described to generate high intensity ultrasound. Sandwich transducers utilizing a bolted stack transducer tuned to a resonant frequency and designed to a half wavelength of the resonant frequency are described in United Kingdom Patent No. 868,784.

High-intensity ultrasonic transducers of the composite or sandwich type typically include front and rear mass members with alternating annular piezoelectric elements and electrodes stacked therebetween. Most such high-intensity transducers are of the pre-stressed type. They employ a compression bolt that extends axially through the stack to place a static bias of about one-half of the compressive force that the piezoelectric transducers can tolerate. When the transducers operate they are designed to always remain in compression, swinging from a minimum compression of nominally zero to a maximum peak of no greater than the maximum compressive strength of the material.

Other embodiments of the prior art utilize a stud that is threadedly engaged with both the first and second resonator to provide compressive forces to the transducer stack. Threaded studs are also known in the prior art for attaching and detaching transmission components to the transducer assembly. See, for example, U.S. Pat. Nos. 5,324,299 and 5,746,756. Such bolts and studs are utilized to maintain acoustic coupling between elements of the sandwich type transducer or any attached acoustic assembly. Coupling is important to maintain tuning of the assembly, allowing the assembly to be driven in resonance.

Sandwich type transducers are relatively high Q devices, and during operation are driven at resonance, and maintained within a relatively narrow frequency range by feedback control methods known in the art. See, for example, U.S. Pat. Nos. 5,630,420 and 5,026,387 which describe systems incorporating and controlling sandwich type transducers.

It is difficult to manufacture sandwich type transducers due to the high Q/narrow resonance range in which these devices operate. It is common to individually tune every transducer at least once during the manufacturing process. Even with the tight tolerances currently available with modern manufacturing processes, tolerance "stack-up" issues present challenges to designers of sandwich type transducers. "Stack-up" issues occur as normal variations due to combining multiple parts, each part having design tolerances, such that variations due to each part sum together to produce a significant variation.

Currently it is known in the art to design the sandwich type transducer longer than desired for a given resonant frequency. During assembly the sandwich type transducer is tested for its resonant frequency, and then the assembly is trimmed shorter to bring it within the desired tuning range. This trimming process often occurs at attachment surfaces, where other acoustic assemblies such as end-effectors are to be attached. It is known that the surface finish quality at attachment surfaces is an important parameter for efficient acoustic assemblies, and the trimming process adds significant manufacturing issues and expense. See, for example, U.S. Pat. No. 5,798,599, which states that transducers require intimate surface contact between adjacent members, and that this intimacy requires surface finishes within 2 Newtonian rings per inch of flatness.

Thus there is a need for a transducer tuning method that does not require trimming at a contact surface. There is also a need for an acoustic assembly method that can account for variations of frequency resonance of individual acoustic assemblies. It would therefore be advantageous to eliminate the need for trimming of acoustic assemblies. It would further be advantageous to be able to design sandwich type transducer components to the desired length for resonance without adding length for tuning due to tolerance "stack-up" issues. It would also be advantageous to provide a method of tuning acoustic assemblies during manufacture that was capable of tuning high Q resonant devices from an existing resonant frequency to a desired resonant frequency. This invention addresses and solves these needs as described below.

SUMMARY OF THE INVENTION

The invention is a method along with the attendant apparatus for manufacturing high power sandwich type ultrasonic transducers and, more particularly, a new method of tuning high power sandwich type ultrasonic transducers without the need for a trimming process. A method in accordance with the present invention includes the steps of assembling a sandwich type ultrasonic transducer, measuring the resonant frequency of the ultrasonic transducer, and selecting from a plurality of tuning elements, whereby a specific tuning element alters the measured resonant frequency of the ultrasonic transducer to a desired resonant frequency after assembly with the ultrasonic transducer. In one embodiment of the present invention the tuning element is a connecting stud that is also used to connect an ultrasonic acoustic assembly to an end-effector.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
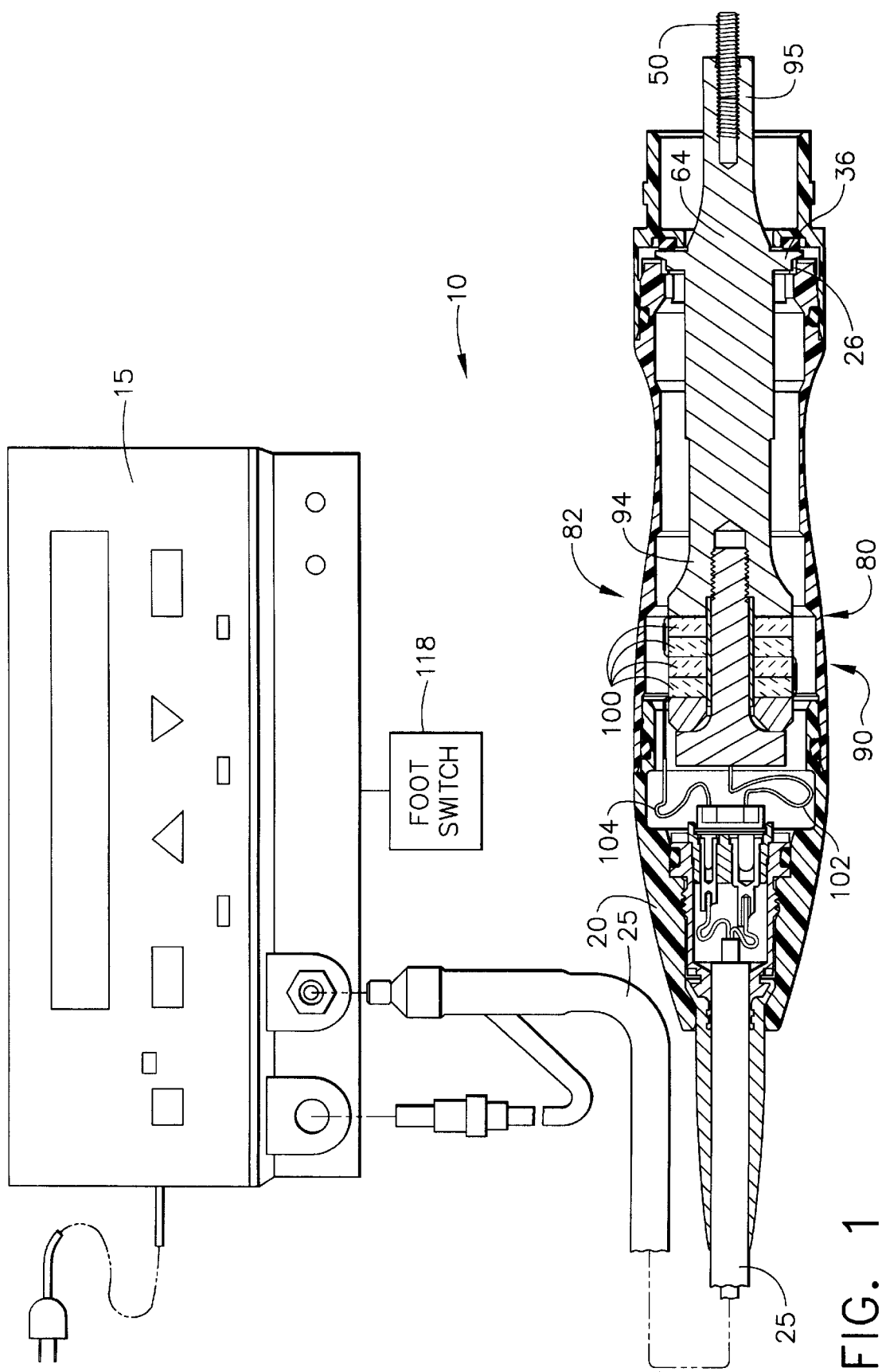
FIG. 1 illustrates a perspective view of an ultrasonic signal generator with a sectioned plan view of a sandwich type ultrasonic transducer and housing in accordance with the present invention.

FIG. 1 illustrates a perspective view of an ultrasonic signal generator 15 with a sectioned plan view of a sandwich type ultrasonic transducer 82 and housing 20 in accordance with the present invention. The transducer 82, which is known as a "Langevin stack", generally includes a transduction portion 90, a first resonator or end-bell 92, and a second resonator or fore-bell 94. The transducer 82 is preferably an integral number of one-half system wavelengths ($n\lambda/2$) in length as will be described in more detail later. An acoustic assembly 80 includes the transducer 82, mount 36, velocity transformer 64 and distal-end 95.

The distal end of end-bell 92 is connected to the proximal end of transduction section 90, and the proximal end of fore-bell 94 is connected to the distal end of transduction portion 90. The first and second resonators 92 and 94 are preferably fabricated from titanium, aluminum, stainless steel, or any other suitable material. Fore-bell 94 and end-bell 92 have a length determined by a number of variables, including the thickness of the transduction section 90, the density and modulus of elasticity of material used end-bell 92 and fore-bell 94, and the resonant frequency of the transducer 82. The fore-bell 94 may be tapered inwardly from its proximal end to its distal end to amplify the ultrasonic vibration amplitude as velocity transformer 64, or alternately may have no amplification.

The transduction portion 90 of the transducer 82 preferably comprises a piezoelectric section of alternating positive electrodes 96 and negative electrodes 98 (see FIG. 2), with piezoelectric elements 100 alternating between the electrodes 96 and 98. The piezoelectric elements 100 may be fabricated from any suitable material, such as, for example, lead zirconate-titanate, lead meta-niobate, lead titanate, or other piezoelectric crystal material. Each of the positive electrodes 96, negative electrodes 98, and piezoelectric elements 100 have a bore extending through the center. The positive and negative electrodes 96 and 98 are electrically coupled to wires 102 and 104, respectfully. Wires 102 and 104 are encased within cable 25 and electrically connectable to generator 15 of ultrasonic system 10.

Figure 2:
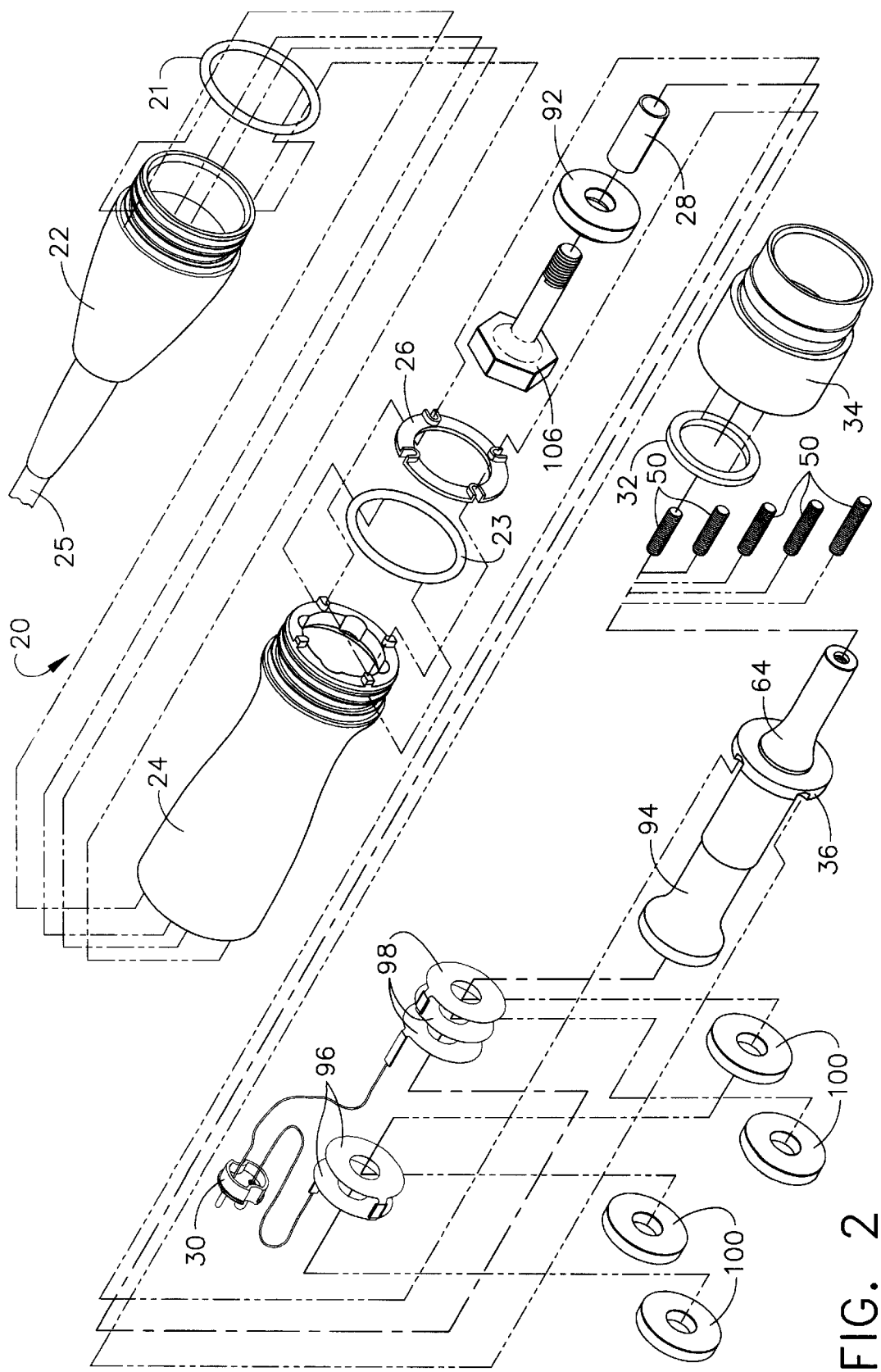
FIG. 2 illustrates an exploded perspective view of a sandwich type ultrasonic transducer and housing in accordance with the present invention.

Referring to FIG. 1, the transducer 82 of the acoustic assembly 80 converts the electrical signal from generator 15 into mechanical energy that results in longitudinal vibratory motion of the ultrasonic transducer 82 and any attached end-effector at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda/4$). FIG. 2 illustrates an exploded perspective view of a handpiece assembly 70 including the ultrasonic transducer 82 and housing 20 in accordance with the present invention. Handpiece assembly 70 includes cable 25, housing 20, acoustic assembly 80, and a selected stud 50. housing 20 includes proximal portion 22, distal portion 24, nose-cone 34, and O-rings 21, 23, and 32. Acoustic assembly 80 includes transducer 82 described above, and ancillary components including acoustic isolator 26, electrode assembly 30, bolt 106, positive electrodes 96, negative electrodes 98, and insulator 28.

Referring to FIGS. 1 and 2, wires 102 and 104 transmit the electrical signal from the generator 15 to electrodes 96 and 98. The piezoelectric elements 100 are energized by an electrical signal supplied from the generator 15 in response to a foot switch 118 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing longitudinal waves of ultrasonic energy. The ultrasonic energy is transmitted through the acoustic assembly 80 to the end-effector.

The piezoelectric elements 100 are conventionally held in compression between end-bell 92 and fore-bell 94 by a bolt 106. The bolt 106 preferably has a head, a shank, and a threaded distal end. The bolt 106 is inserted from the proximal end of end-bell 92 through the bores of end-bell 92, the electrodes 96 and 98, and piezoelectric elements 100. The threaded distal end of the bolt 106 is screwed into a threaded bore in the proximal end of fore-bell 94.

In order for the acoustic assembly 80 to deliver energy all components of acoustic assembly 80 must be acoustically coupled. The distal end of the transducer 82 may be acoustically coupled to the proximal end of an ultrasonic end-effector by a threaded connection such as stud 50.

The components of the acoustic assembly 80 are preferably acoustically tuned such that the length of any assembly is an integral number of one-half wavelengths (n$\lambda$/2), where the wavelength $\lambda$ is the wavelength of a pre-selected or operating longitudinal vibration drive frequency $f_d$ of the acoustic assembly 80, and where n is any positive integer. It is also contemplated that the acoustic assembly 80 may incorporate any suitable arrangement of acoustic elements.

Figure 3:
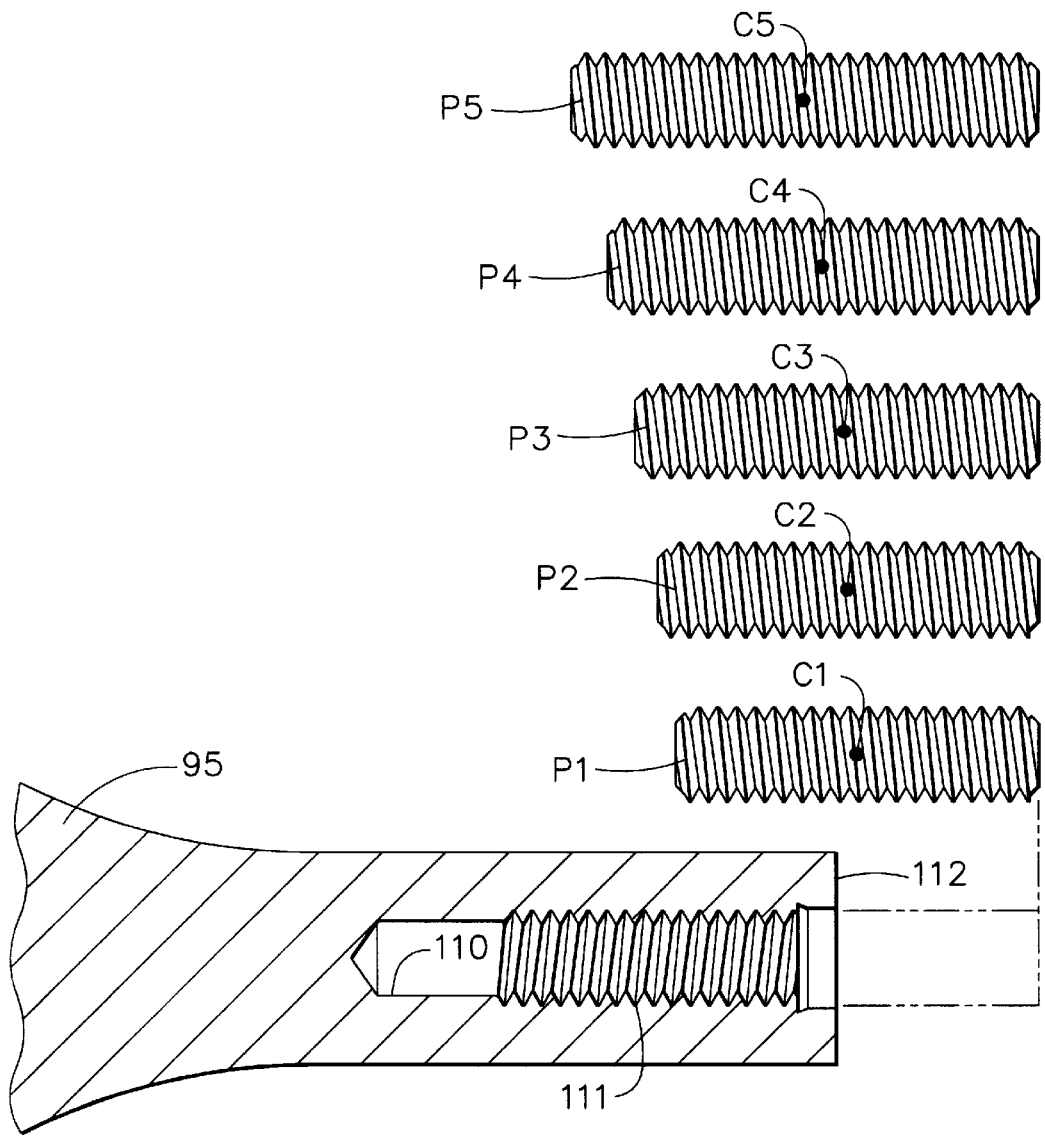
FIG. 3 illustrates a sectioned plan view of the distal-end of an acoustic assembly along with a plurality of attachment studs of differing lengths in accordance with the present invention.

FIG. 3 illustrates a sectioned plan view of the distal-end 95 of acoustic assembly 80 along with the plurality of attachment studs 50 of differing lengths in accordance with the present invention. Distal-end 95 includes bore 110, threaded portion 111, and terminal face 112. Studs 50 may be sorted by size or mass such as, for example, P1 through P5 as described below in Table 1.

A method of manufacture and method of tuning have been developed to eliminate the need to trim acoustic assembly 80 at, for example, terminal face 112 during the manufacturing process. Utilizing the methods of the present invention, acoustic assembly 80 may be designed to have an acoustic length (n$\lambda$/2). "Stack-up" resonant frequency discrepancies of acoustic assembly 80 may be corrected by proper selection of a tuning element such as, for example, stud 50, when the relationship between stud size or mass and the frequency effect on acoustic assembly 80 of insertion of stud 50 into threaded portion 111 of bore 110 is understood. It can be appreciated that other tuning elements may be utilized to correct for resonant frequency variations, such as, for example, selection from a plurality of fore-bells 94, end bells 92, or other ancillary components, each of which having varying masses.

TABLE 1

| Stud 50 sorted into lengths and associated tuning ranges | | | | | |
|---|---|---|---|---|---|
| Transducer Frequency | 55375 +/−25 | 55440 +/−40 | 55540 +/−60 | 55650 +/−50 | 55750 +/−50 |
| P Level | P1 | P2 | P3 | P4 | P5 |
| Stud Length (inches) | .400 stud | .420 stud | .445 stud | .475 stud | .515 stud |

Table 1 is provided as an example of frequency ranges and stud 50 lengths for an embodiment of the present invention. A measured transducer 82 frequency is shown in the first row, along with a frequency deviation range correctable by the stud 50 disclosed in each column. It may be appreciated that a transducer 82 may be designed to have a resonant frequency of 55,540 Hertz, corresponding to the column containing P Level (P3). If the measured resonant frequency during assembly is within +/−60 Hertz of 55,540 Hertz, then a 0.445 inch stud may be inserted to keep transducer 82 within its design limits for frequency. As the measured resonant frequency of transducer 82 deviates above or below the designed frequency, an appropriate stud 50 length may be selected from Table 1 to compensate for the deviation and bring transducer 82 within the desired resonant frequency range.

Figure 4:
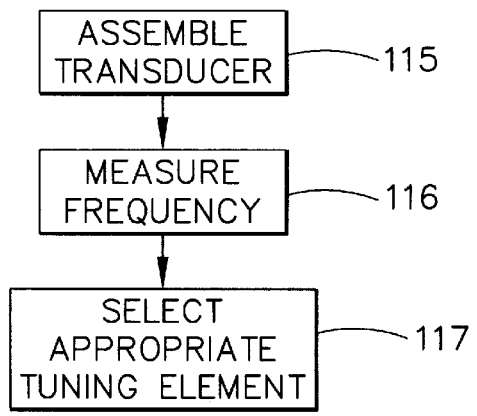
FIG. 4 is a flow chart of an embodiment of an ultrasonic transducer assembly or tuning method in accordance with the present invention.

FIG. 4 is a flow chart of an embodiment of ultrasonic transducer 82 assembly or tuning method in accordance with the present invention. Acoustic assembly 80 may be designed to have a resonant frequency $f_d$, and an effective acoustic length of (n$\lambda$/2). However, tolerance "stack-up" variations in material properties of components, or other aspects of the assembly may cause acoustic assembly 80 to deviate from its designed resonant frequency as shown above in Table 1. During the assembly process ultrasonic transducer 82 or the entire acoustic assembly 80 may be measured for resonant frequency. Deviations from the desired resonant frequency may be corrected by proper selection and insertion of a tuning stud 50.

The flow chart of FIG. 4 includes the steps of:
A) assembling a sandwich type ultrasonic transducer 82, designated as process 115;
B) measuring the resonant frequency of the ultrasonic transducer 82, designated as process 116; and
C) selecting a stud 50 from a plurality of Studs P1 through P5, whereby the length of a selected stud can alter the measured resonant frequency of the ultrasonic transducer to a desired resonant frequency, designated as process 117.

In another embodiment of the present invention, studs 50 of equal size but varying densities may be used. For example studs P1 through P3 may be of equal length, but stud P1 may be manufactured from Aluminum, stud P2 may be manufactured from stainless steel, and stud P3 may be manufactured from Tungsten. The assembly or tuning process may select from one of the three studs of different densities to compensate for differences in resonant frequency.

A further embodiment of the present invention may be appreciated when considering a simple resonator model. The ability of a mass located around an anti-node of vibration to alter resonant frequency may be envisioned as analogous to a mass hanging at the end of a spring. If the mass is displaced and released, the mass spring system will vibrate at a resonant frequency. If the mass is increased, the resonant frequency will decrease. If the mass is decreased, the resonant frequency will increase.

Using the above analogy, as the stud size or mass increases, the overall resonant frequency of acoustic assembly 80 may be decreased from a measured resonant frequency to a desired resonant frequency within a range useable to correct for manufacturing variations. Likewise as the mass selected is decreased, the resonant frequency would be increased.

The ability of an added mass to alter the frequency of an acoustic assembly 80 changes as the mass deviates from an anti-node of acoustic vibration. If a mass is added at a node of vibration its effect on, the resonant frequency is due primarily to any stiffness it adds near the node. In the spring/mass analogy, the added mass at a node is analogous to increasing the spring rate. Alternately, if that same mass is located at an anti-node of vibration, its effect on the resonant frequency is due to the increased mass in the mass/spring analogy. The effect of the mass' exact location about (within $\lambda$/4) an anti-node is much less pronounced than increasing or decreasing mass near an anti-node, but is still sufficient to tune within a limited frequency range. Changing location of a single mass with respect to its location about an anti-node of vibration has a similar effect as changing the mass located at the anti-node. This is due to the effectiveness (of the mass to alter frequency) being highest exactly at an anti-node, and its effectiveness decreasing as a cosine function as it is displaced from the anti-node.

Thus it is also possible to correct for resonant frequency variation by proper location of the center of mass of a tuning element such as stud 50. As illustrated in FIG. 3, studs P1 through P5 have centers of mass C1 through C5 respectively. If stud 50 is inserted into threaded portion 111 of bore 110 such that stud 50 extends from terminal face 112 at a consistent length regardless of which stud P1 through P5 is selected, then the location of the center of mass of stud 50 within distal-end 95 will vary as the length of stud 50 varies, as illustrated in FIG. 3.

Figure 5:
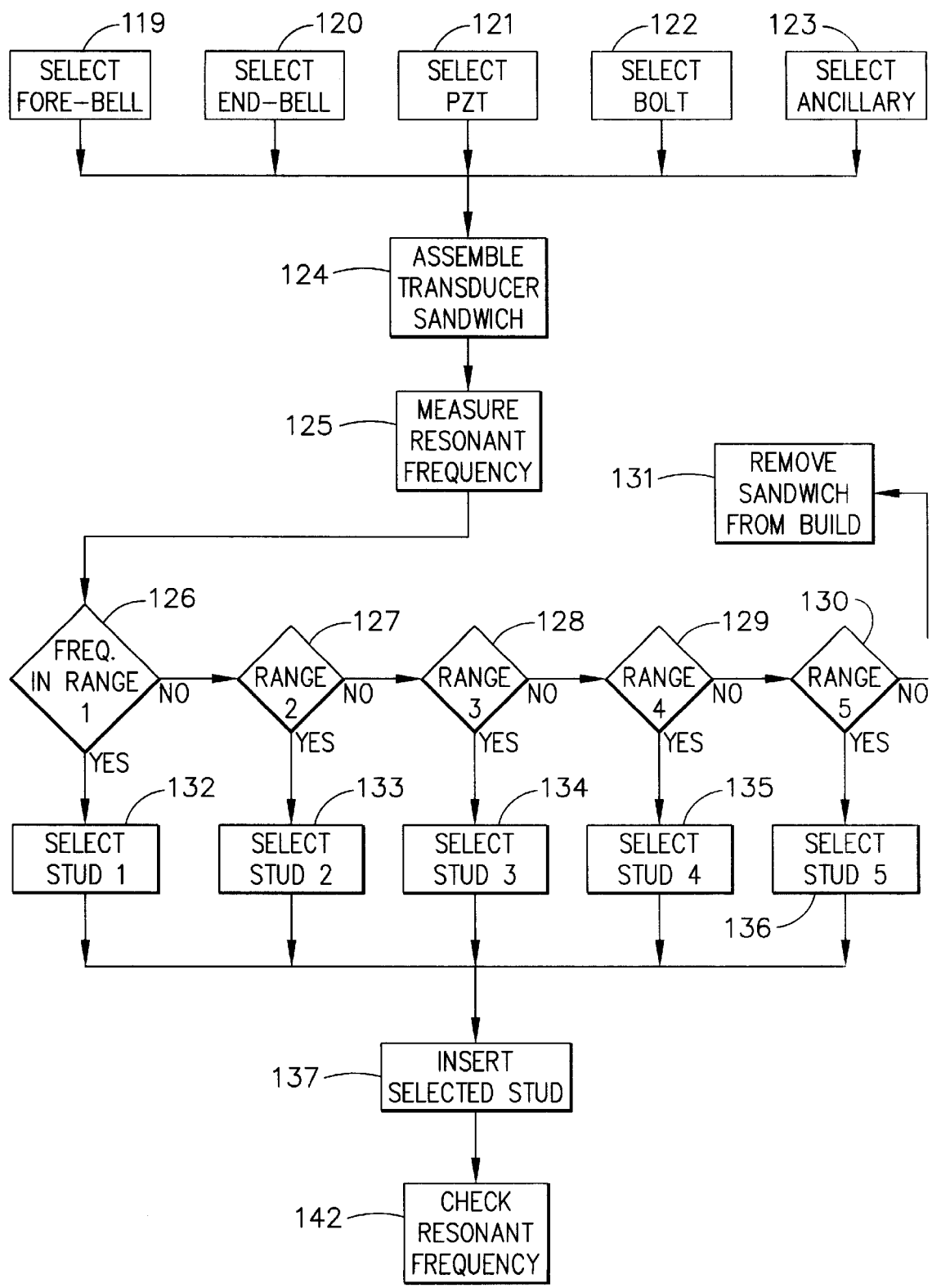
FIG. 5 is a flow chart of an embodiment of an ultrasonic transducer assembly or tuning method in accordance with the present invention.

FIG. 5 is a flow chart of an embodiment of an ultrasonic transducer assembly or tuning method in accordance with the present invention. The flow chart of FIG. 5 includes the steps of selecting at least one piezoelectric element, wherein the piezoelectric element includes a central opening, designated as process 121; selecting an end-bell, wherein the end-bell includes a central opening, designated as process 120; selecting a fore-bell, the fore-bell including: a proximal surface; a distal surface; and a body separating the proximal surface and the distal surface; wherein the proximal surface includes a first threaded bore, and wherein the distal surface includes a second threaded bore, designated as process 119; selecting ancillary pieces, designated as process 123; assembling a transducer sandwich, designated as process 124; measuring the resonant frequency, designated as process 125; determining the appropriate range, designated as decisions 126 through 130; selecting from a plurality of studs according to the measured frequency rangy, designated processes 132 through 136 respectively to decisions 126 through 130; inserting the appropriate stud into the second threaded bore of the distal surface of the fore-bell, designated as process 137; and checking that the proper correction was accomplished by re-measuring resonance, designated as process 142. Assemblies falling outside acceptable resonant frequency ranges are removed from the build as illustrated in process 131.

Figure 6:
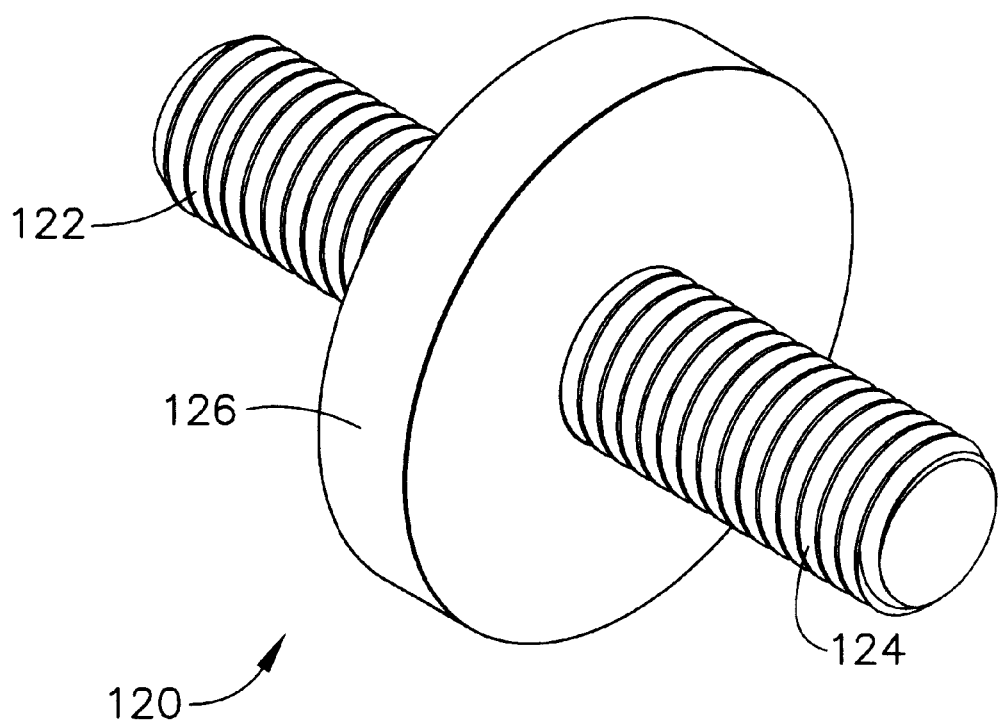
FIG. 6 is a perspective view of an alternate embodiment of a tuning stud in accordance with the present invention.

FIG. 6 is a perspective view of an alternate embodiment of a tuning stud 120 in accordance with the present invention. Tuning stud 120 comprises a proximal threaded portion 122, a central non-threaded portion 126, and a distal threaded portion 124. Central non-threaded portion 126 may be altered in length or diameter to vary the amount of resonant frequency shift desired when tuning stud 120 is inserted into threaded portion 111 of bore 110 illustrated in FIG. 3. Central non-threaded portion 126 may also comprise materials of differing density, thereby altering the mass of tuning stud 120. It can be appreciated that central non-threaded portion 126 may also be a washer placed onto stud 50 to perform as tuning stud 120.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic transducer assembly comprising:
   a transducer housing, said transducer housing comprising a central opening;
   a transducer stack, said transducer stack comprising:
      a first and second resonator section, a piezoelectric section between said
      first and second resonator sections;
   a velocity transformer, said velocity transformer comprising a proximal end and a distal end, said proximal end coupled to said second resonator section, said distal end comprising:
      a bore, said bore extending from said distal end of said velocity transformer into said velocity transformer, said bore comprising a threaded portion;
   a mount, said mount retaining said transducer within said central opening of said housing;
   a stud, said stud inserted into said threaded portion of said bore, wherein said studs comprises:
   a proximal threaded portion;
   a central non-threaded portion adjacent to said proximal threaded portion; a distal threaded portion adjacent to said non-threaded portion, wherein said central portion has a length defined between said proximal threaded portion and said distal threaded portion, whereby said length is selected to tune said transducer assembly from a first frequency to a second desired frequency.

2. An ultrasonic transducer assembly comprising:
   a transducer housing, said transducer housing comprising a central opening;
   a transducer stack, said transducer stack comprising:
      a first and second resonator section, a piezoelectric section between said first and second resonator sections, said second resonator section comprising a proximal end and a distal end, said proximal end coupled to said piezoelectric section, said distal end comprising:
         a bore, said bore extending from said distal end of said second resonator section into said second resonator section, said bore comprising a threaded section;
   a mount, said mount retaining said transducer within said central opening of said housing;
   a stud, said stud inserted into said threaded portion of said bore, wherein said stud has a length, whereby said length is selected to tune said transducer assembly from a first frequency to a second desired frequency.

* * * * *